(12) United States Patent
Barone

(10) Patent No.: US 6,613,078 B1
(45) Date of Patent: Sep. 2, 2003

(54) MULTI-COMPONENT ENDOLUMINAL GRAFT ASSEMBLY, USE THEREOF AND METHOD OF IMPLANTING

(76) Inventor: Hector Daniel Barone, Maza 1948, Buenos Aires (AR)

(*) Notice: Subject to any disclaimer, the term of this patent is extended or adjusted under 35 U.S.C. 154(b) by 118 days.

(21) Appl. No.: 09/631,011

(22) Filed: Aug. 2, 2000

(51) Int. Cl.[7] .................................................. A61F 2/06
(52) U.S. Cl. ...................... 623/1.13; 623/1.32; 606/194
(58) Field of Search ............................... 623/1.13, 1.14, 623/1.16, 1.3–1.32, 1.44; 128/898; 606/191, 192, 194, 195, 198

(56) References Cited

U.S. PATENT DOCUMENTS

| | | | |
|---|---|---|---|
| 4,922,905 A | | 5/1990 | Strecker ...................... 606/195 |
| 5,464,449 A | * | 11/1995 | Ryan et al. ..................... 600/36 |
| 5,667,523 A | * | 9/1997 | Bynon et al. ................ 606/194 |
| 5,716,365 A | * | 2/1998 | Goicoechea et al. ......... 606/195 |
| 5,948,017 A | * | 9/1999 | Taheri ........................ 623/1.14 |
| 6,168,619 B1 | * | 1/2001 | Dinh et al. ................. 623/1.13 |
| 6,325,823 B1 | * | 12/2001 | Horzewski et al. ......... 623/1.16 |
| 6,331,191 B1 | * | 12/2001 | Chobotov .................. 623/1.21 |
| 6,334,866 B1 | * | 1/2002 | Wall .......................... 623/1.11 |

FOREIGN PATENT DOCUMENTS

| | | |
|---|---|---|
| WO | 8303752 | 11/1983 |
| WO | 9015582 | 6/1990 |

* cited by examiner

*Primary Examiner*—David J. Isabella
*Assistant Examiner*—Urmi Chattopadhyay
(74) *Attorney, Agent, or Firm*—Norris McLaughlin & Marcus (57) ABSTRACT

A multi-component stent-graft assembly for repairing a lesion in a blood vessel, preferably a thoracic dissecting aneurysm, the assembly comprising a frame stent that is affixed to the vessel, in the healthy portions of the vessel and extending along the entire lesion of the vessel, and a stent-graft which is affixed against the inside of the frame stent, the stent-graft being located at the desired locations within the affected portion of the vessel no matter the vessel wall is in conditions to retain the stent-graft, because the retention will be provided by the frame stent.

20 Claims, 7 Drawing Sheets

Fig. 7

MULTI-COMPONENT ENDOLUMINAL GRAFT ASSEMBLY, USE THEREOF AND METHOD OF IMPLANTING

BACKGROUND OF THE INVENTION

1. Field of the Invention

The present invention relates to a graft assembly for repairing blood vessels, preferably vessels affected by lesions in the vessel wall, more preferably lesions of the type known as dissecting aneurysms, and particularly relates to a graft assembly, the use thereof and method for intraluminal implanting the graft assembly into a blood vessel affected by a lesion wherein no firm walls of the vessel are available to get a firm and stable implantation of a conventional graft. The invention is particularly suited for repairing thoracic dissecting aneurysms, although it is not limited thereto.

2. Description of the Prior Art

It is well known that blood vessels are affected by diseases generating deformations and damages in the vessel wall, particularly the aortic vessel which may be subject to aneurysm formation and severe atherosclerotic disease resulting in multiple sclerosis. In addition, the blood vessels may be affected by other types of damages like occlusions. In any of these afflictions it is common to carry out a repairing method in the compromised region of the vessel in order to preserve the health or even the life of the patient. Previously, such afflictions were repaired by traditional surgery in order to reach the affected vessel, making corresponding incisions in the patient's body and through the vessel to implant, within the vessel, a graft or prosthesis in order to replace the portion of the vessel affected by the disease.

Nowadays, most of the above affections and lesions are treated by implanting one or more prosthesis, particularly endoluminal stent-grafts, into the affected artery or vein. The endoluminal stent-graft is typically comprised of a metallic stent, such as a mesh-type stent, the stent being of the self-expanding or balloon expandable type, and a liner or tubular graft material which is affixed, by sutures for example, to the inside or the outside of the metallic stent. The stent-graft in a collapsed condition is delivered to the affected portion of the vessel via a catheter and, once in the correct position, the stent-graft is deployed, either by means of a balloon or by letting the self expanding stent to resiliently expand upon moving out of the catheter, in order to cause the stent-graft to be firmly affixed against the vessel wall, inside the blood vessel.

Many endoluminal grafts are well known and widely used in the art. U.S. Pat. No. 4,922,905 relates to a catheter and discloses a tubular endoprosthesis device having a wall structure comprised of a tube-like, knitted open fabric of loosely interlocked loops of metallic filament material, said tube-like fabric being radially inwardly deformed relative to its as-knit form and is capable of progressive permanent deformation with attendant radial expansion by means of the catheter to attach the endoprosthesis inside a blood vessel to be repaired.

WO 83/03752 to Wallsten, Hans Ivar, discloses a prosthesis comprising a one-piece expandable tubular body to be inserted into a vascular vessel.

WO 90/15582 to Trout, Hugh, discloses an aortic graft comprising a substantially cylindrical graft material with attachment means which comprise a plurality of post and hook assemblies to provide firm attachment of the aortic graft against the aortic wall.

The above referred stent-grafts may be used satisfactorily provided that a healthy and firm wall of the vessel is available surrounding the lesion so that the stent-graft may be affixed to such firm wall in stable and fixed conditions. It is common to find lesions extending along a large portion or length of the affected vessel with a bifurcation, namely an inlet or outlet vessel branch, located in the affected portion, between the healthy portions of the wall, or close to the afflicted portion. Under these circumstances if a short stent-graft is implanted, the same has an insufficient length to extend along the entire afflicted portion and, while an end of the stent-graft may be located over the healthy portion of the vessel wall, for obtaining a proper retention, the opposite end will be in the lesion where no reliable retention is available. If a larger stent is implanted to have both ends of the graft implanted a healthy and firm wall parts, while covering the entire length of the afflicted portion, it will occlude any bifurcation, namely inlets or outlets of vessel branches located in the lesion-affected portion of the vessel.

It would be therefore desirable to develop a graft for use in repairing blood vessels with lesions wherein the wall of the vessel is not in conditions to receive and firmly retain an implanted graft in the desired and necessary location inside the vessel. It would also be desirable to have a graft to selectively repair the lesions in the vessel wall without occluding any outlet or inlet of a branch in or close to the lesion.

SUMMARY OF THE INVENTION

It is therefore an object of the present invention to provide a multi-component stent-graft assembly for repairing a lesion in a blood vessel, preferably a thoracic dissecting aneurysm, the assembly comprising a frame stent that is affixed to the vessel, in the healthy portions of the vessel and extending along the entire lesion of the vessel, and a stent-graft which is affixed against the inside of the frame stent, the stent graft being located at the desired locations within the affected portion of the vessel no matter the vessel wall is or not in conditions to retain the stent-graft, because the retention will be provided by the frame stent.

It is also an object of the present invention to provide a multi-component endoluminal graft assembly for repairing blood vessels affected by one or more lesions, the multi-component graft assembly comprising an outer frame stent for endoluminaly affixing to the blood vessel, and at least one hollow tubular stent-graft for being arranged coaxially within said outer frame stent and affixed to the outer frame stent.

It is still another object of the present invention to provide a multi-component endoluminal graft assembly for repairing blood vessels affected by one or more lesions, the multi-component graft assembly comprising an outer frame stent, either self-expanding or a balloon expandable stent, and at least one hollow tubular stent-graft comprising an inner stent, and a graft made of fabric or textile material and coaxially arranged over the inner stent, wherein the outer frame stent is to be endoluminaly affixed to the blood vessel and the stent-graft is to be arranged coaxially within said outer frame stent and affixed to the outer frame stent once the outer frame stent is expanded and affixed against the vessel, whereby the textile graft is to remain sandwiched between the outer frame stent and the inner stent.

It is even another object of the present invention to provide a use of the above multi-component endoluminal graft assembly, wherein the multi-component graft is endoluminaly implanted in a blood vessel affected by at least one lesion, wherein the outer frame stent is affixed to the vessel and the at least one stent-graft is coaxially arranged within the outer frame stent and affixed to the outer frame stent.

It is a further object of the present invention to provide a use of the above multi-component endoluminal graft assembly, wherein the multi-component graft is endolumlnaly implanted in a blood vessel affected by at least one lesion, wherein he outer frame stent is affixed to the vessel and the at least one stent-graft is coaxially arranged within the outer frame stent and affixed to the outer frame stent, wherein the stent-graft comprises a graft axially over at least one inner stent and the graft remains sandwiched between the at least one inner stent and the outer frame stent.

It is a further object of the present invention to provide a multi-component endoluminal graft assembly for repairing blood vessels affected by one or more lesions, the multi-component graft comprising a self-expanding endoluminal outer frame stent made of resilient wire, and at least one hollow tubular stent-graft comprising an inner balloon-expandable stent, and a graft made of a fabric material and coaxially arranged within or outside the inner stent, wherein the self-expanding outer frame stent is to be endoluminaly affixed to the blood vessel and the stent-graft is to be arranged coaxially within said self-expanding outer frame stent and affixed to said self-expanding outer frame stent once the self-expanding outer frame stent is expanded and affixed against the vessel, whereby, if the graft is outside the inner stent the fabric graft remains sandwiched between the self-expanding outer frame stent and the inner balloon-expandable stent.

It is still a further object of the invention to provide a use of the above multi-component endoluminal graft assembly comprising a self-expanding endoluminal outer frame stent made of resilient wire, and at least one hollow tubular stent-graft comprising an inner balloon-expandable stent and a graft either within or outside the inner stent, wherein the multi-component graft is endoluminaly implanted in a blood vessel affected by at least one lesion, wherein the outer frame stent is affixed to the vessel and the stent-graft is coaxially within the outer frame stent and affixed to the outer frame stent, whereby, if the graft is outside the inner stent, the graft remains sandwiched between the inner stent and the outer frame stent.

It is even an additional object of the invention to provide a method of implanting a multi-component endoluminal graft assembly in a blood vessel for repairing at least one lesion, the method comprising the steps of:

provinding an outer frame stent, either a self-expanding or a balloon expandable stent, inserting the outer frame stent within the blood vessel at a location for endoluminaly covering at least the lesion and expanding the outer frame stent so as to be deployed at said location and affixed against the blood vessel, providing at least one hollow tubular stent-graft;

inserting the stent-graft coaxially within the expanded and implanted outer frame stent and expanding the at least one stent-graft so as to be deployed and affixed against at least one portion of the outer frame stent.

It is a further object of the invention to provide a method of implanting a multi-component endoluminal graft assembly in a blood vessel for repairing at least one lesion, the method comprising the steps of:

providing an outer frame stent, either a self-expanding or a balloon expandable stent, inserting the outer frame stent within the blood vessel at a location for endoluminaly covering at least the lesion and expanding the cuter frame stent so as to be deployed at said location and affixed against the blood vessel, providing at least one hollow tubular stent-graft comprising:

at least one inner stent, and a graft coaxially arranged over the at least one inner stent, and inserting the stent-graft coaxially within the expanded and implanted outer frame stent and expanding the at least one stent-graft so as to be deployed and affixed against at least one portion of the outer frame stent, whereby the graft remains sandwiched between the outer frame stent and the at least one inner stent.

The above and other objects, features and advantages of this invention will be better understood when taken in connection with the accompanying drawings and description.

BRIEF DESCRIPTION OF THE DRAWINGS

The present invention is illustrated by way of example in the following drawings wherein.

DESCRIPTION OF THE PREFERRED EMBODIMENTS

Figure 1:
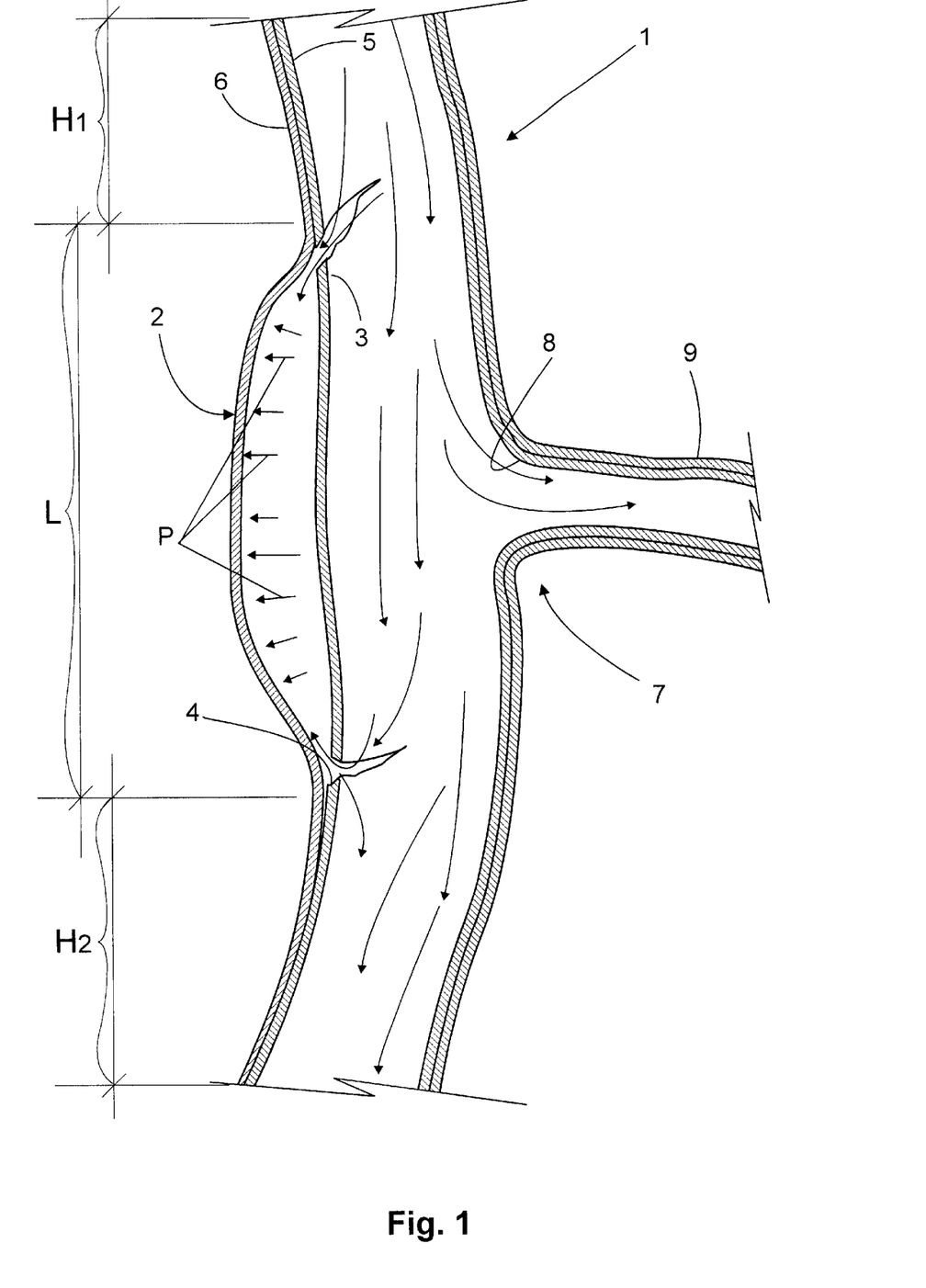
FIG. 1 shows a cross-sectional view of a blood vessel affected by a dissecting aneurysm, with two ruptures in an inner layer of the vessel wall, and a vessel branch or bifurcation shown at the right side of the vessel.

Now referring in detail to the drawings it may be seen from FIG. 1 a thoracic aortic vessel generally indicated by numeral reference 1, affected by a thoracic dissecting aneurysm 2 consisting of at least one rupture 3, with two ruptures 3, 4 being shown as an exemplary affection of the vessel. The dissecting aneurysm 2 consist of a delamination, that is the separation into constituent layers, of the vessel wall. While only two layers have been illustrated in the present application, the walls of blood vessels are comprised of several layers and only two layers are shown for clarity purposes. The dissecting aneurysm begins with a small rupturing 3 in an inner layer 5 of the vessel wall, the blood pressure then causes the blood to enter the rupture and flow through the vessel wall between the inner layer and an outer layer 6, thus delaminating the wall into separated layers 5, 6 and forming an abnormally dilated wall or aneurysm 2. The aneurysm defines a lesion extending along an affected portion or length indicated by the reference L. At the ends of portion L, the vessel has its wall in healthy conditions which portions, with purposes of description, will be identified as healthy wall portions H1 and H2. A collateral vessel or bifurcation 7 is shown at the right side of vessel 1, with an ostium 8 of a vessel branch 9.

If aneurysm 2 is not treated, the delamination due to the continuous blood flow is not interrupted and the lesion may progress or extend beyond the limits of length L. In addition, the blood flow exerts excessive pressure, indicated by the short arrows P, against outer layer 6, which effect, combined with the progression of the lesion, leads to the rupturing outer layer 6 with ensuing fatal hemorrhaging in a very short time.

Many attempts have been made to prevent and avoid the high mortality due to the above described abnormality, many of the attempts involving surgical techniques with associated high risk for the patient, and others, less traumatic, consisting of acceding the vessel intraluminally to insert and install inside the vessel a graft to exclude the lesion from the blood circulatory system. When installing the graft in the vessel the graft must be firmly attached to those healthy or uninjured portions of the vessel wall, in good conditions to provide a safe attachment, that is a firm anchoring and sealing coupling between the graft and the vessel.

The healthy portions, however, are not frequently available at short distances from the lesion, in other words, the healthy portions of the vessel wall are not close to each other, therefore, short stent-grafts which should be long enough to cover and repair the lesion are not long enough to have their ends anchored in the spaced apart healthy portions. To overcome this situation, longer stent-grafts have been manufactured and installed within the affected vessels to extend along the entire length of the lesion in order to reach the healthy portions of the vessel. More detailed reference to these techniques of the prior art will be made in connection to FIGS. 2 and 3.

Figure 2:
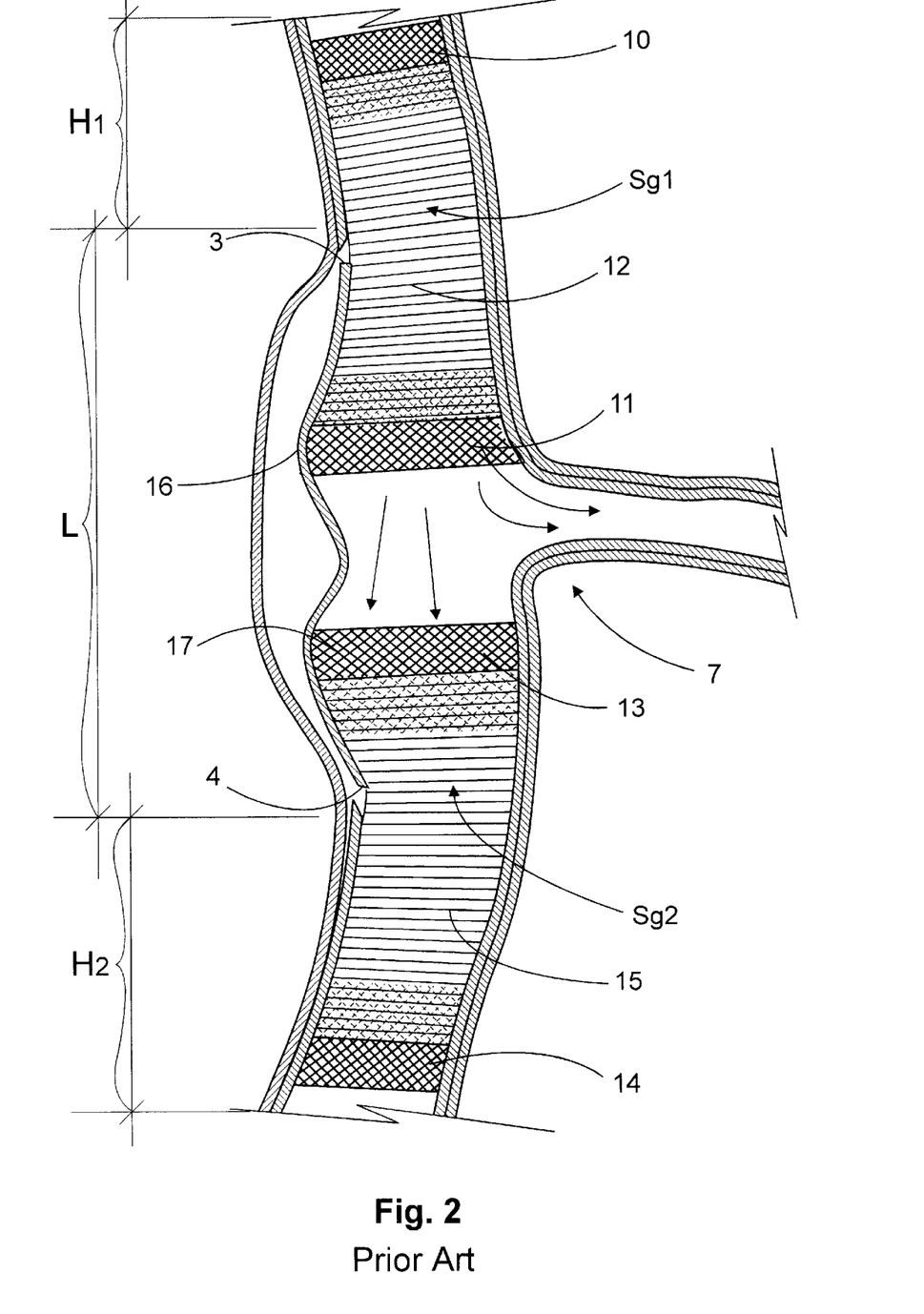
FIG. 2 shows a cross-sectional view of the blood vessel of FIG. 1 with two spaced apart short stent-grafts of the prior art implanted at the locations where the vessel wall is ruptured.

FIG. 2 shows one of the above approaches provided by the prior art. In order to avoid occluding ostium 8, two short stent-grafts SG1 and SG2 are implanted inside the vessel, each one at the location of corresponding ruptures 3, 4. Stent-graft SG1 typically comprises an upper stent 10, a lower stent 11 and a textile liner, or graft, 12. In like manner, stent-graft SG2 comprises an upper stent 13, a lower stent 14 and a liner 15. The purpose of liners 12, 15 is to occlude the leakage through ruptures 3, 4, and they are retained against the vessel wall by stents 10, 11, 13, 14, which are made of wire and implanted against the vessel wall either by balloon or by self-expanding. Therefore, the stents remain anchored in the vessel provided that the wall of the vessel is in good structural and resistant conditions to offer the stent the necessary support. As it will be readily appreciate by any person skilled in the art, while upper stent 10 is anchored against healthy portion H1 of the vessel, lower stent 11 has been implanted by expansion against the affected portion L of the vessel, which portion is not in conditions to provide a firm anchoring of the stent. The same drawback appears in relation to stent-graft SG2, having its stent 13 implanted in the region within lesion L. As it has been indicated by references 16, 17, the affected wall yields against the expansion of stents 11, 13, without offering resistance and support, the layer 5 excessively dilating in portions 16, 17, generally leading to the dislodgment of the stent-graft or, worst, to the rupturing of the layer.

Figure 3:
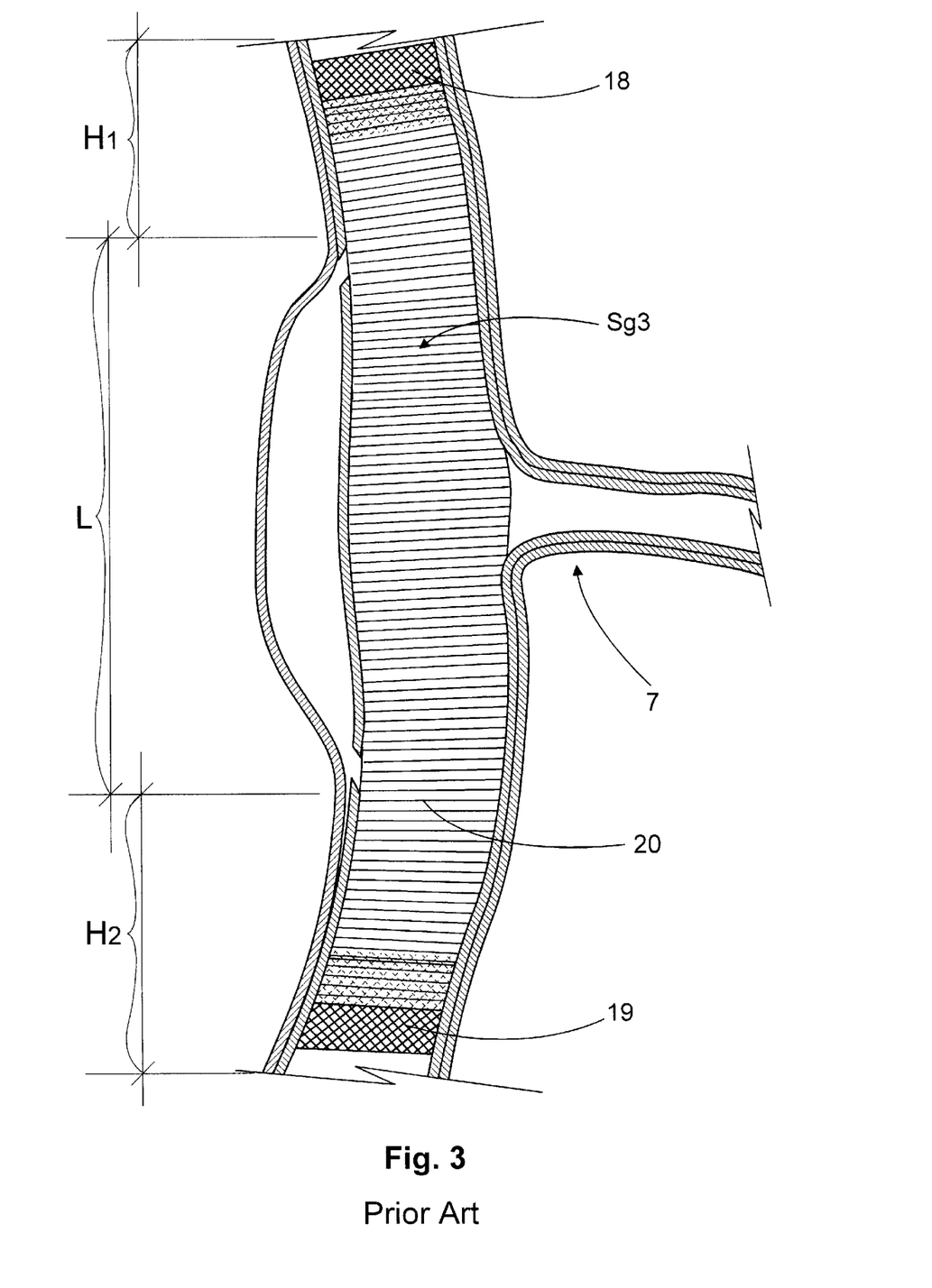
FIG. 3 shows a cross-sectional view of the blood vessel of FIG. 1 with one long stent-graft of the prior art extending along the entire aneurysm with the purpose of being firmly affixed to the healthy ends of the vessel, repairing the ruptures at the vessel wall, but undesirably occluding the ostium of the vessel branch.

In order to get a firm anchoring of the prosthesis within the vessel a longer Stent-graft SG3, illustrated in FIG. 3, has been implanted according to another approach of the prior art. Prosthesis or stent-graft SG3 comprises typically two end stents 18, 19 and a textile liner or graft 20 that is conventionally affixed, by sutures for example, to the stents. Once stents 18, 19 are firmly anchored inside the vessel, graft 20 extend along the lesion covering ruptures 3, 4, thus isolating the lesion from the blood flow, which blood now flows into graft 20, and repairing the vessel. Differing from short stent-grafts SG1 and SG2, stent-graft SG3 is longer enough to extend along the entire length L and reach the healthy portions H1 and H2 of the vessel to get a firm anchoring of both ends of the stent-graft. While a firm retention of the prosthesis is obtained, ostium 8 is unduly occluded by the graft, thus interrupting the blood flow through branch 9 and resulting in the dead of tissues and parts of the patient's body irrigated by this branch.

Figure 4:
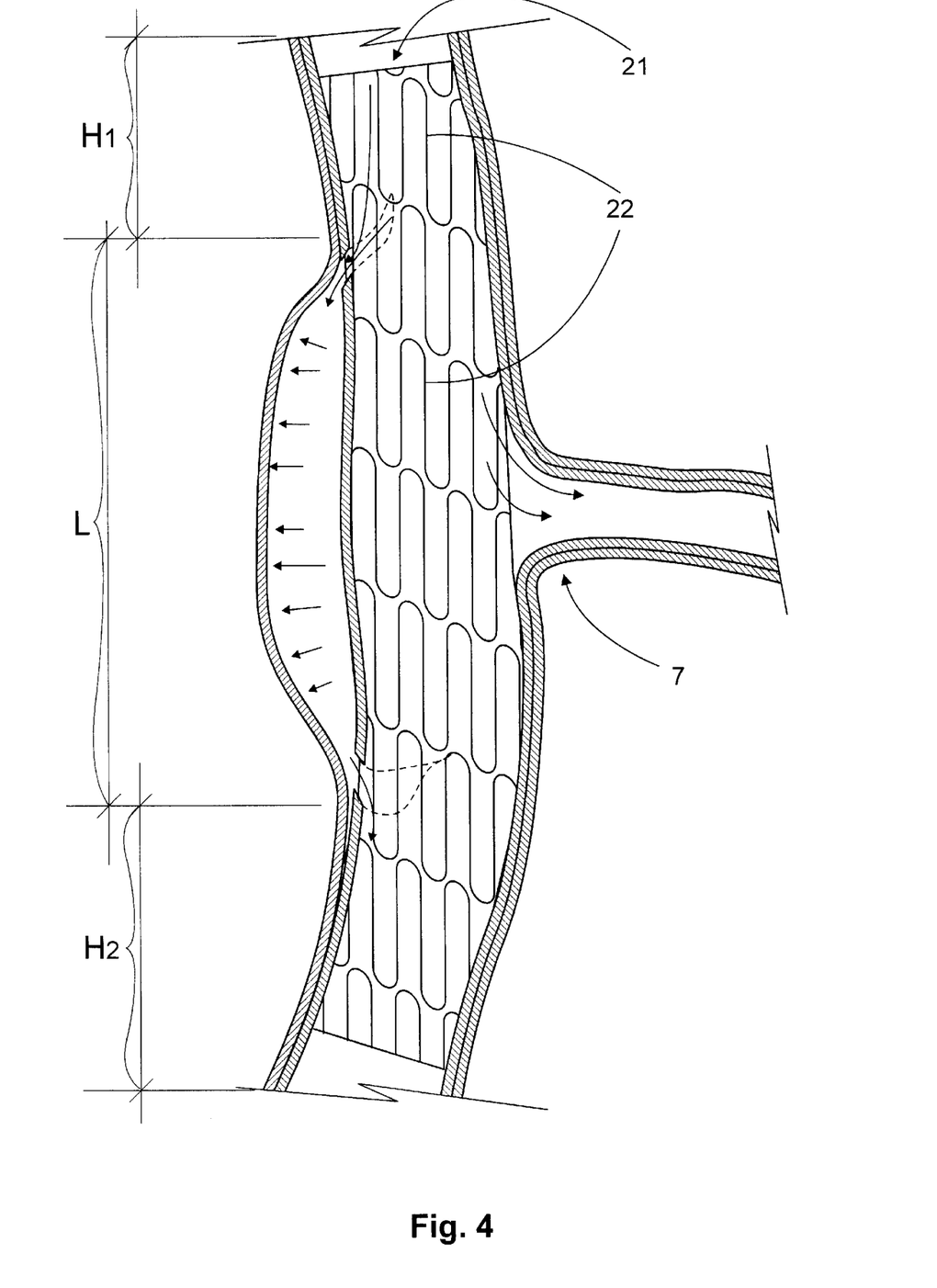
FIG. 4 shows a cross-sectional view of the blood vessel of FIG. 1 with a frame stent according to the invention implanted, also according to the invention, to provide the affected vessel wall with a resistant structure to receive and affix the inventive stent-graft.
Figure 5:
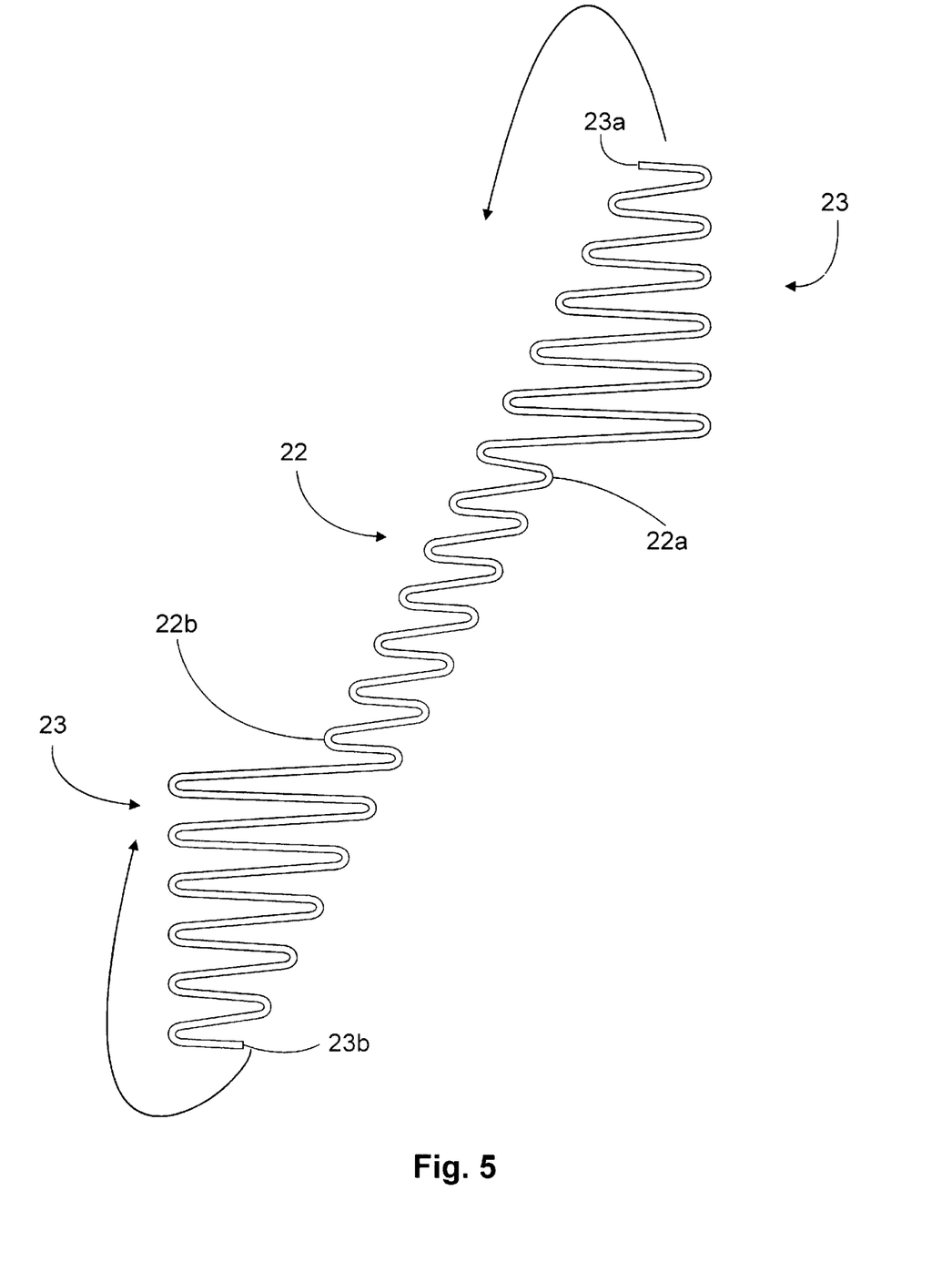
FIG. 5 shows the frame stent of FIG. 4, in a unwounded condition, before being hellically wounded into the tubular configuration of FIG. 4.

To overcome the above explained drawbacks of the prior art, the present invention provides for a new graft assembly shown in FIGS. 4–7. According to the invention, a multi-component endoluminal graft assembly is provided for repairing blood vessels affected by one or more lesions, preferably aneurysms, more preferably dissecting aneurysms. The inventive graft or prosthesis assembly comprises, according to a preferred embodiment of the invention, an outer frame stent 21 comprising a metallic structure made of wire 22, or a mesh, for example, of a memory alloy. The wire is preferably nitinol, but it may be of biomedical stainless steel, or any other proper material. The wire of the stent ii preferably configured in zig-zag, or may have a generally sinusoidal configuration, and is helically wound into a tubular shape as shown in FIG. 4. The stent structure may be manufactured as a metallic strip, as shown in FIG. 5, consisting of a zig-zag configured wire defining three portions, with a central portion 22 and two end portions 23, the wire in the corresponding portions having different configurations, as shown, in order to helically, wound the wire into a cylinder configuration, for example as it is indicated by the arrows at the ends 23, and obtain a tubular frame stent as shown in FIG. 4. Upon folding the wire, vertex 22a is preferably placed to meet, or to be close to, vertex 23a, and vertex 23b is put in coincidence with, or close to, vertex 22b. The remaining vertexes are preferably close to, or in coincidence with, each other. Frame stent 21 has a preferred diameter of 25–50 mm.

Frame stent 21 is preferably a self-expanding stent, however, it could comprise a balloon-expandable metallic structure. According to the invention, stent 21 is implanted within vessel 1 as shown in FIG. 4, with the ends of the stent firmly anchored in the healthy regions of the vessel, namely in portions H1 and H2, extending along the entire lesion length L, without occluding any ostium 8 or branch in the length of the region. The frame stent implanted in the illustrated configuration remains firmly anchored inside the vessel and provides a supportive and resistant structure within the vessel for replacing the supporting function of the vessel wall along portion L. With the frame stent now forming a supportive non impervious wall, occluding and repairing grafts may be implanted, according to the invention, and as it will be disclosed in connection to FIG. 7, in selective locations of the vessel with the purpose of occluding only such portions of the vessel that are necessary to be occluded and leaving without occlusion such other parts wherein the blood flow must be maintained.

Figure 6:
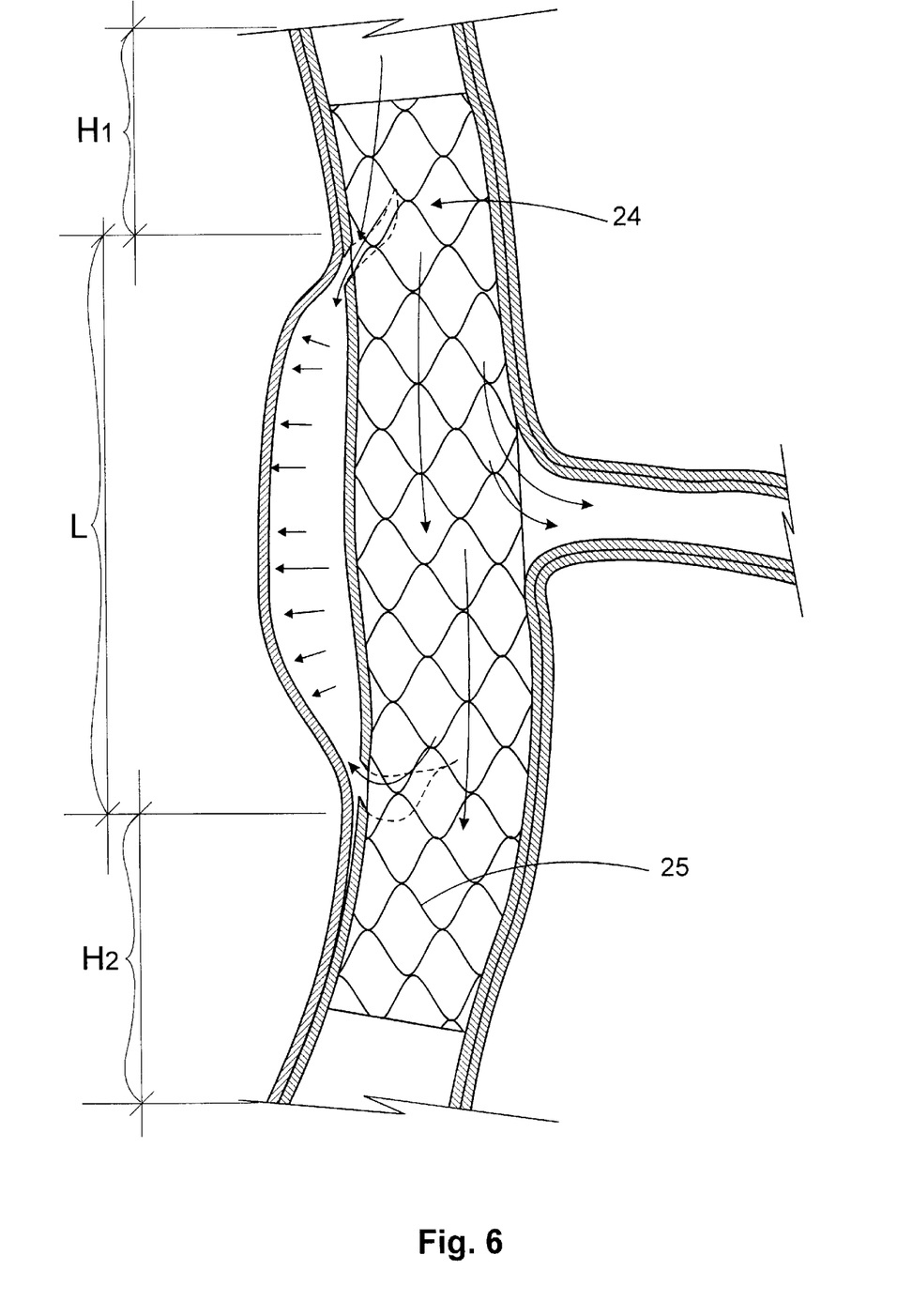
FIG. 6 shows a cross-sectional view of the blood vessel of FIG. 1 with an alternative frame stent according to the invention implanted in the affected vessel prior to receive and affix the inventive stent-graft.

FIG. 6 shows a view similar to the one of FIG. 4, but with another type of frame stent 24 consisting of a wire structure having a rhombus repetitive pattern 25, which pattern may be any one available in the market. While the stent structure is preferably self-expandable, it may be of any other type, such as balloon-expandable, provided that the same provides a supportive structure once expanded and implanted in the vessel.

Figure 7:
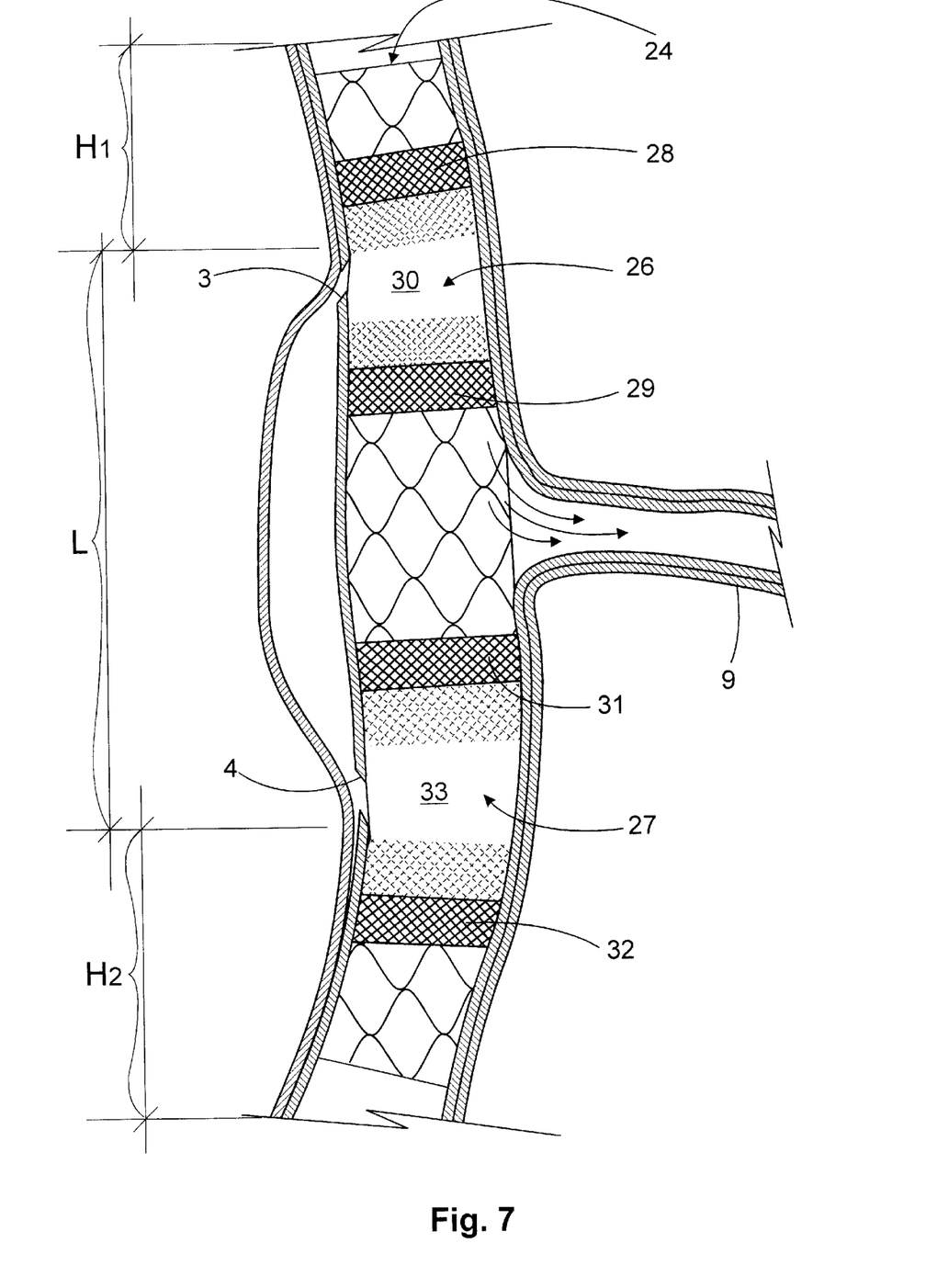
FIG. 7 shows a cross-sectional view of the blood vessel of FIG. 1 with two spaced apart short stent-grafts of the invention implanted at the locations where the vessel wall is ruptured but affixed to the inventive frame stent of FIG. 6, thus occluding the ruptures in the wall but keeping the flow of he blood through the ostium of the vessel branch.

FIG. 7 shows the entire graft assembly of the invention implanted inside the vessel of FIG. 1. The inventive assembly comprises, in addition to the frame stent, at least one hollow tubular stent-graft, with two stent-grafts 26, 27 being illustrated to show a preferred application of the invention. Stent-graft 26 comprises an upper inner stent 28, a lower inner stent 29 and a liner or graft 30 affixed to the inner stents, only one inner stent, however, may be used in replacement of both upper and lower stents. Stent-graft 27 comprises an upper inner stent 31, a lower inner stent 32 and a liner or graft 33, only one inner stent, however, may be used in replacement of both upper and lower stents. Grafts 30 and 33 may be affixed to the inner surface or the outer surface of inner stents 28, 29, 31 and 32, that is the graft may be within or outside the inner stents. If the graft is outside the inner stent, which arrangement is the preferred one, the graft will remain sandwiched between he inner stent and the frame stent when implanted. Grafts 30, 33 are preferably made of a tubular deformable fabric or textile material, either a compliant material or a non-compliant material, and are coaxially arranged over the corresponding inner stents. For the purposes of this application the term "fabric" must be understood as comprising any textile, film or materials such as DACRON, polyester, polyethylene terephthalate (PET), polytetrafluoroethylene (PTFE), or any other suitable material. Preferably the material is compliant and PTFE. The graft may be a woven or non-woven material, a mesh or textile, for example a warp-knit, atlas-knit or weft-knit. The inner stents may be self-expanding stents made of resilient wire or may be balloon-expandable stents. Preferably, stents 28, 29, 31, 32 are balloon-expandable made of 316L steel. Stent-grafts 26, 27 may be identical or may have distinct lengths, different textile liners or different stents.

According to the invention, stent-grafts 26, 28 will be implanted in the proper locations to repair and occlude the ruptures 3, 4 without occluding ostium 8 of branch 9, or any other ostium, branch or bifurcation involved in the affected region L. While stents 28, 29, 31, 32 are implanted within portion L, the same remain firmly anchored against frame stent 24, no matter whether the wall of the vessel in that region is firm or dilated. Thus, the outer frame stent is endoluminaly affixed to the blood vessel and each stent-graft 26, 27 is arranged coaxially within outer frame stent 24 and affixed to the outer frame stent simultaneously with the implanting of the frame stent or once the outer frame stent has been expanded and affixed against the vessel. As explained above, if the graft is affixed to the outer surface of the inner stent or stents, the fabric grafts will remain sandwiched between the outer frame stent and the corresponding inner stent(s). Thus, the use of the graft assembly according to the invention provides a safety solution to repair a blood vessel affected by one or more lesions.

Also according to the invention a method for implanting the graft assembly is provided. The inventive method comprises the step of providing an outer frame stent, for example frame stent 21, within a catheter or introducer, the stent being collapsed in an appropriate pattern to be accommodated within the introducer. By means of an incision in the patient's body the introducer is inserted into an elected blood vessel within the body until reaching the affected portion L of an affected vessel. Once in the correct position, the frame stent is deployed out of the introducer, either by means of a balloon, or by letting the outer self-expanding frame stent to expand and to be anchored and affixed against the blood vessel, as it is shown in FIGS. 4 and 6. Then, one or more stent-grafts 26 and/or 27, depending of the lesion to be repaired, are supplied, also by using a introducer, for example, into the already installed frame stent. The stent-graft is coaxially located inside the expanded and implanted outer frame stent and is expanded so as to be deployed and affixed against at least one portion of the outer frame stent, whereby textile or fabric graft 30 and/or 33 is sandwiched between the outer frame stent and the corresponding inner stent 28, 29, 31, 32.

Once a self-expanding outer frame stent is used the step of expanding the stent comprises permitting the stent to resiliently expand against the blood vessel. If the stent-graft is a balloon-expandable stent-graft, the step of expanding the stent-graft comprises inflating one or more balloons to expand the stent-graft against the outer frame stent. Once the outer frame stent is a balloon-expandable stent the step of expanding the frame stent comprises inflating one or more balloons to expand the outer frame stent against the blood vessel. If the stent-graft is a self-expanding stent-graft, the step of expanding the stent-graft comprises permitting the stent-graft to resiliently expand against the outer frame stent.

While preferred embodiments of the present invention have been illustrated and described, it will be obvious to those skilled in the art that various changes and modifications may be made therein without departing from the scope of the invention as defined in the appended claims.

I claim:

1. A multi-component endoluminal graft assembly for repairing a blood vessel affected by one or more lesions, wherein the one or more lesions exist in a region proximate to one or more ostiums of branches of the vessel, the assembly being formed for insertion into the vessel in a manner such that the one or more lesions are repaired without the blood flow through the one or more branches being blocked by the assembly, the multi-component graft assembly comprising:

an outer frame stent for endoluminaly affixing to the blood vessel, the outer frame stent forming a supportive non-impervious wall permitting blood flow therethrough; and at least one hollow tubular stent-graft, independent of the outer frame stent, adapted to be coaxially locatable within said outer frame stent after the outer frame stent is deployed within a blood vessel and affixable to the outer frame stent at a selective position between ends of the outer frame stent, a total length of all stent-grafts in the assembly being less than a length of the outer frame stent by at least a length of the one or more ostiums;

whereby the outer frame stent is structured to extend, when in use, all along the one or more lesions of the vessel and over any of the one or more ostiums located between the ends of the outer frame stent, and the at least one tubular stent-graft extends, when in use, into the outer frame stent along a selective portion of the frame stent, but not into a region of the one or more ostiums, for occluding only the one or more lesions of the vessel and leaving the one or more ostiums unoccluded for maintaining a free blood flow within the vessel and the one or more branches.

2. The multi-component endoluminal graft assembly of claim 1, wherein
the at least one hollow tubular stent-graft comprises:
at least one inner stent; and
a graft coaxially arranged over the at least one inner stent; wherein
the at least one stent-graft is affixed to the outer frame stent once the outer frame stent is expanded and affixed against the vessel, whereby the graft remains sandwiched between the outer frame stent and the at least one inner stent.

3. The multi-component endoluminal graft assembly of claim 2, wherein the outer frame stent is a self-expanding metallic structure.

4. The multi-component endoluminal graft assembly of claim 3, wherein the outer frame stent is made of a wire of nitinol.

5. The multi-component endoluminal graft assembly of claim 3, wherein the at least one inner stent is a self-expanding stent made of resilient wire.

6. The multi-component endoluminal graft assembly of claim 3, wherein the at least one inner stent is made of wire and is a balloon-expanding stent.

7. The multi-component endoluminal graft assembly of claim 2, wherein the outer frame stent comprises a metallic structure made of a zig-zag configured wire helically wound into a tubular shape.

8. The multi-component endoluminal graft assembly of claim 2, wherein the outer frame stent comprises a balloon-expandable metallic structure.

9. The multi-component endoluminal graft assembly of clam 2, wherein the graft comprises a tubular deformable fabric material, the material being selected from the group consisting of polyester, polyethylene terephthalate (PET) and polytetrafluoroethylene (PTFE), the material being affixed to the at least one inner stent.

10. The multi-component endoluminal graft assembly of claim 2, wherein the graft comprises a tubular deformable textile material, the material being selected from the group consisting of a mesh formed by one of a woven textile material, a compliant material, a non-compliant material, a warp-knit, an atlas-knit and a weft-knit.

11. The multi-component endoluminal graft assembly of claim 1, wherein the outer frame stent is a self-expanding endoluminal stent made of resilient wire, and the at least one hollow tubular stent-graft comprises at least one inner balloon-expandable stent and a graft coxially arranged over the at least one inner stent, wherein
the stent-graft is affixed coaxially within said self-expanding outer frame stent once the self-expanding outer frame stent is expanded and affixed against the vessel, whereby the graft remains sandwiched between the self-expanding outer frame stent and the at least one inner balloon-expandable stent.

12. The multi-component endoluminal graft assembly of claim 11, wherein the outer frame stent is made of a wire of nitinol.

13. The multi-component endoluminal graft assembly of claim 11, wherein the outer frame stent comprises a metallic structure made of a zig-zag configured wire helically wound into a tubular shape.

14. The multi-component endoluminal graft assembly of claim 11, wherein the graft comprises a tubular deformable fabric material, the material being selected from the group consisting of polyester, polyethylene terephthalate (PET) and polytetrafluoroethylene (PTFE), the material being affixed to the at least one inner stent.

15. The multi-component endoluminal graft assembly of claim 11, the graft comprises a tubular deformable textile material, the material being selected from the group consisting of a mesh formed by one of a woven textile material, a compliant material, a non-compliant material, a warp-knit, an atlas-knit and a weft-knit.

16. A method of implanting a multi-component endoluminal graft assembly in a blood vessel for repairing one or more lesions in the vessel, wherein the one or more lesions exist in a region proximate to one or more ostiums of branches of the vessel, the method comprising the steps of, in order:
providing an outer frame stent forming a supportive non-impervious wall permitting blood flow therethrough;
inserting the outer frame stent into the blood vessel at a location extending over the one or more lesions and any of the one or more ostiums proximate to the one or more lesions, and expanding the outer frame stent so as to be deployed at said location and affixed against the blood vessel;
providing at least one hollow tubular stent-graft, independent of the outer frame stent;
inserting the at least one tubular stent-graft coaxially within the expanded and implanted outer frame stent and expanding the at least one tubular stent-graft so as to be deployed and affixed into the outer frame stent at a selective position between ends of the outer frame stent but not into a region of any of the one or more ostiums located between the ends of the outer frame stent;
whereby the outer frame stent is implanted all along the one or more lesions of the vessel and over any of the one or more ostiums and the at least one tubular stent-graft is installed into the outer frame stent along said selective position occluding only the one or more lesions of the vessel and leaving the one or more ostiums unoccluded for maintaining a free blood flow within the vessel and the one or more branches.

17. The method of claim 16, wherein the at least one hollow tubular stent-graft comprises:
at least one inner stent; and
graft coaxially arranged over the at least one inner stent; and
the at least one stent-graft is affixed against the outer frame stent in a manner that the graft remains sandwiched between the outer frame stent and the at least one inner stent.

18. The method of claim 17, wherein the outer frame stent is a self-expanding stent and the step of expanding the outer frame stent comprises permitting the outer frame stent to resiliently expand against the blood vessel.

19. The method of claim 18, wherein the at least one stent-graft is a balloon-expandable stent-graft and the step of expanding the at least one stent-graft comprises inflating a balloon to expand the at least one stent-graft against the outer frame stent.

20. The method of claim 18, wherein the at least one stent-graft is a self-expanding stent-graft and the step of expanding the at least one stent-graft comprises permitting the at least one stent-graft to resiliently expand against the outer frame stent.

* * * * *